US011458015B2

(12) United States Patent
Zhu et al.

(10) Patent No.: US 11,458,015 B2
(45) Date of Patent: *Oct. 4, 2022

(54) PERFUSION BALLOON DESIGN

(71) Applicant: Edwards Lifesciences Corporation, Irvine, CA (US)

(72) Inventors: Yidong M. Zhu, Irvine, CA (US); Erik Bulman, Lake Forest, CA (US); Baigui Bian, Laguna Niguel, CA (US); Sam Sok, Santa Ana, CA (US); Pu Zhou, Dove Canyon, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 412 days.

This patent is subject to a terminal disclaimer.

(21) Appl. No.: 16/791,976

(22) Filed: Feb. 14, 2020

(65) Prior Publication Data

US 2020/0179116 A1 Jun. 11, 2020

Related U.S. Application Data

(63) Continuation of application No. 15/260,192, filed on Sep. 8, 2016, now Pat. No. 10,561,496.
(Continued)

(51) Int. Cl.
*A61F 2/24* (2006.01)
*A61M 25/10* (2013.01)

(52) U.S. Cl.
CPC .......... *A61F 2/2433* (2013.01); *A61F 2/2418* (2013.01); *A61M 25/1002* (2013.01);
(Continued)

(58) Field of Classification Search
CPC .............. A61M 25/10; A61M 25/1002; A61M 25/1011; A61M 2025/1086;
(Continued)

(56) References Cited

U.S. PATENT DOCUMENTS 5,108,370 A 4/1992 Walinsky
5,232,446 A 8/1993 Arney
(Continued)

FOREIGN PATENT DOCUMENTS

WO 2008005405 A2 1/2008
WO 2012118508 A1 9/2012
(Continued)

*Primary Examiner* — Ryan J. Severson
*Assistant Examiner* — Mikail A Mannan
(74) *Attorney, Agent, or Firm* — Meunier Carlin Curfman LLC; Joel B. German

(57) ABSTRACT

Disclosed herein are designs for improved inflatable structures for use during minimally invasive cardiovascular procedures. These inflatable structures facilitate the perfusion of blood through an anatomical structure, such as a heart valve, during the cardiovascular procedure. The inflatable structures are formed of a plurality of balloons arranged radially around a central location. The plurality of balloons form a lumen through which blood flows. Each balloon of the plurality is shaped or configured to stabilize the adjacent balloons, limiting their movement relative to each other. For example, some embodiments can feature balloons with a keystone shape that limits movement of the balloons inward toward the lumen. Some implementations can also include a support coil running through the lumen. The support coil holds enables the lumen to be open to perfusion even in the early stages of balloon inflation.

19 Claims, 16 Drawing Sheets

Related U.S. Application Data

(60) Provisional application No. 62/219,607, filed on Sep. 16, 2015.

(52) U.S. Cl.
CPC . *A61M 25/1011* (2013.01); *A61M 2025/1086* (2013.01); *A61M 2025/1095* (2013.01); *A61M 2025/1097* (2013.01)

(58) Field of Classification Search
CPC .. A61M 2025/1059; A61M 2025/1097; A61M 2025/1072; A61M 2025/1095; A61F 2/2427; A61F 2/958; A61F 2/2433
See application file for complete search history.

(56) References Cited

U.S. PATENT DOCUMENTS

| | | |
|---|---|---|
| 5,458,575 A | 10/1995 | Wang |
| 5,470,313 A | 11/1995 | Crocker et al. |
| 5,749,852 A | 5/1998 | Schwab et al. |
| 5,776,099 A | 7/1998 | Termulis |
| 5,865,801 A | 2/1999 | Houser |
| 6,245,040 B1 | 6/2001 | Inderbitzen et al. |
| 6,872,215 B2 | 3/2005 | Crocker et al. |
| 7,740,609 B2 | 6/2010 | Rowe et al. |
| 8,221,349 B2 | 7/2012 | Auyoung et al. |
| 9,023,101 B2 | 5/2015 | Krahbichler |
| 2004/0073165 A1 | 4/2004 | Musbach et al. |
| 2007/0213663 A1 | 9/2007 | Wang |
| 2011/0144742 A1 | 6/2011 | Madrid et al. |
| 2011/0190867 A1 | 8/2011 | Vonderwalde et al. |
| 2012/0083809 A1 | 4/2012 | Drasler et al. |
| 2012/0109179 A1 | 5/2012 | Murphy et al. |
| 2013/0226131 A1 | 8/2013 | Bacino et al. |
| 2013/0289607 A1 | 10/2013 | Pedersen et al. |
| 2015/0141917 A1 | 5/2015 | Tilson et al. |
| 2015/0272732 A1* | 10/2015 | Tilson ................. A61F 2/958 623/2.11 |

FOREIGN PATENT DOCUMENTS

| | | |
|---|---|---|
| WO | 2013184945 A1 | 12/2013 |
| WO | 2014063039 A1 | 4/2014 |

* cited by examiner

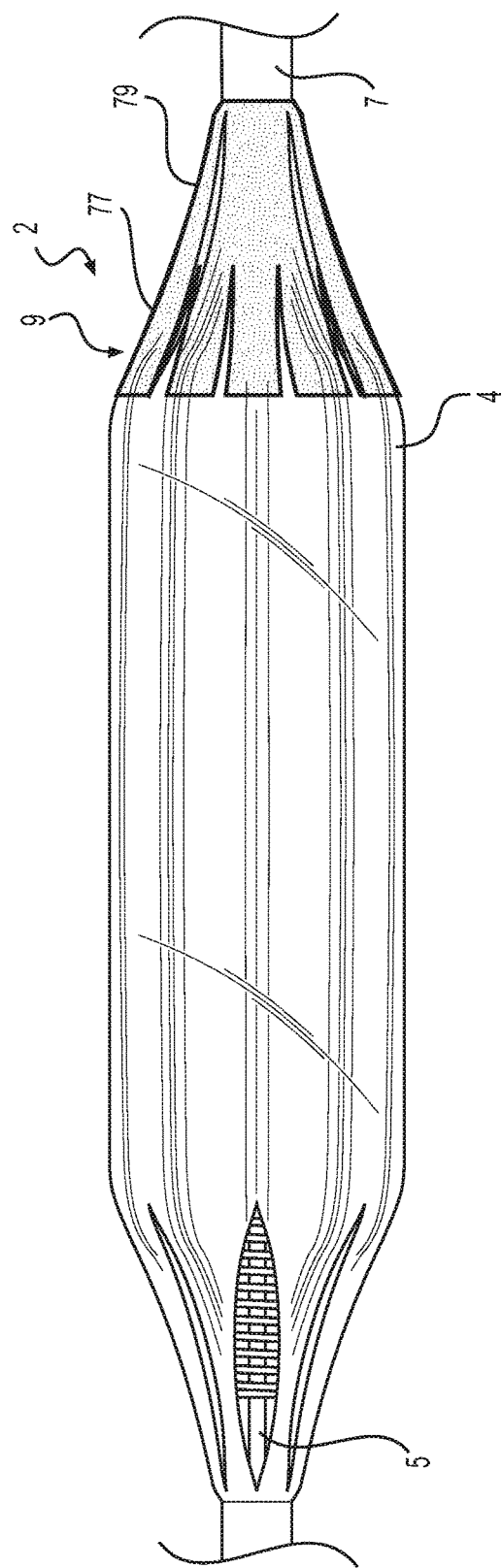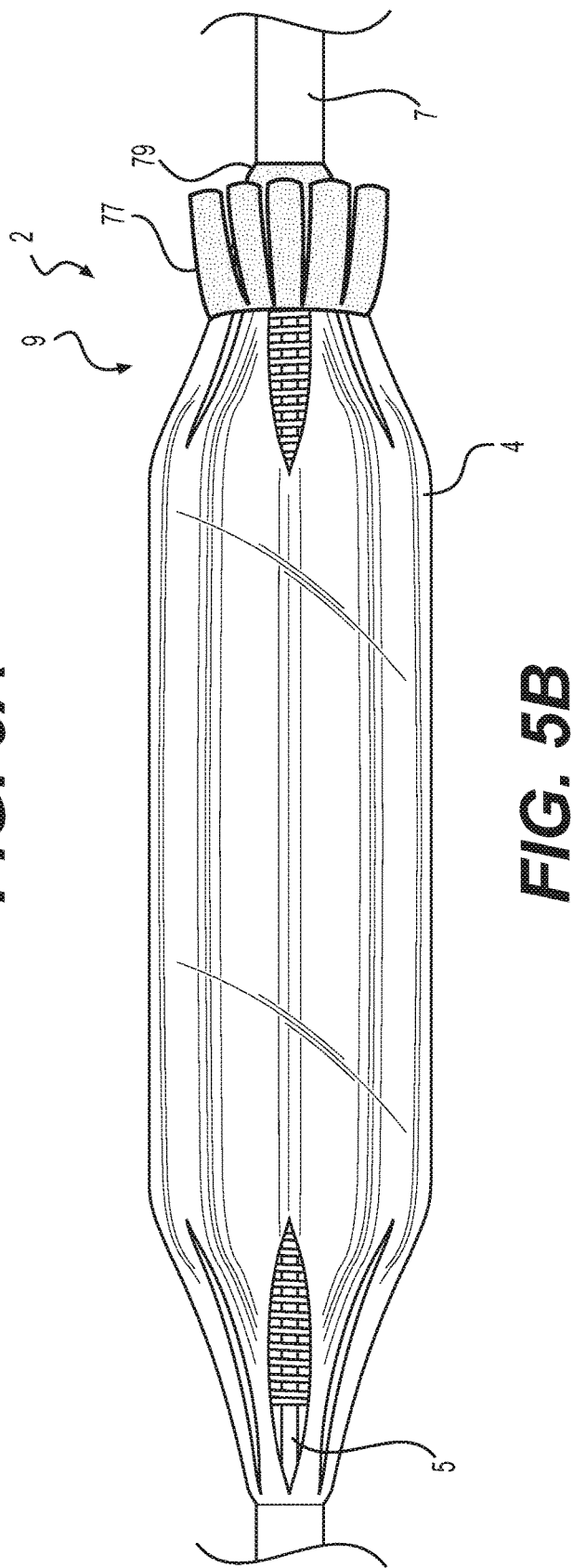

PERFUSION BALLOON DESIGN

RELATED APPLICATIONS

This application is a continuation of U.S. application Ser. No. 15/260,192, filed Sep. 8, 2016, which claims the benefit of U.S. Provisional Application No. 62/219,607, filed Sep. 16, 2015. Each of these applications is incorporated by reference in its entirety for all purposes.

FIELD OF THE INVENTION

The present invention relates generally to devices and methods for promoting perfusion of blood through a cardiac valve during valve repair procedures, and more particularly, to delivery balloons that permit the flow of blood therethrough while delivering a prosthetic implant to a native cardiac valve.

BACKGROUND

Heart valve disease is a serious problem that involves the malfunction of one or more valves of the heart. The malfunction can manifest itself in a variety of manners. For example, valve stenosis is the calcification or narrowing of a native heart valve. As a result, the native heart valve is not able to completely open and blood flow through the native valve is impeded or restricted. Another example of heart valve disease is valve insufficiency. Valve insufficiency is the failure of a native heart valve to close properly to prevent leaking, or backflow, of blood through the valve.

Various methods have been developed to treat heart valve disease. Some of these methods require a balloon member that is expanded within the native heart valve. For example, a balloon member can be used in a valvuloplasty procedure where the balloon member is positioned within the native heart valve and expanded to increase the opening size (i.e., flow area) of the native heart valve and thereby improve blood flow. Another procedure that can be performed is a valve replacement, in which a native heart valve is replaced by an artificial heart valve. The implantation of an artificial heart valve in the heart can also involve the expansion of a balloon member in the valve annulus. For example, the balloon member can be used to increase the size of the native valve prior to implantation of the artificial valve and/or it can be used to expand and deploy the artificial valve itself.

Currently, a single balloon is typically used to deploy the heart valve or stent in minimally invasive cardiovascular procedures. The expansion of a balloon member within a native valve or other vascular passageway, however, can temporarily block or restrict blood flow through the passageway. Furthermore, in the case of valve replacement, the positioning of the artificial heart valve may be complicated by the buildup of pressure in the left ventricle. For example, the blocked blood flow will create a strong force against the balloon while the heart is still pumping during the procedure, decreasing the stability of the implant and making it difficult to position the heart valve. Accordingly, valvuloplasty and valve replacement procedures, and other similar procedures which utilize expandable balloon members, must generally be performed quickly so that the balloon member is inflated for only a brief period. Rapid ventricular pacing procedures may be employed to increase the stability, but this procedure can only be carried out for a limited time span.

Accordingly, a need exists for improved devices that enable the patient's blood to flow through the passageway while the procedure is taking place. Such devices would increase the precision of device placement and reduce the risk of injury to the patient.

SUMMARY

Disclosed herein are designs for improved inflatable structures for use during minimally invasive cardiovascular procedures. These inflatable structures facilitate the perfusion of blood through an anatomical structure, such as a heart valve, during the cardiovascular procedure. The inflatable structures are formed of a plurality of balloons arranged circumferentially around a central location or axis. The plurality of balloons in this arrangement thus form a lumen through which blood flows. Each balloon of the plurality is shaped or configured to stabilize the adjacent balloons, limiting their movement relative to each other. For example, some embodiments may feature balloons with a keystone shape that limits movement of the balloons inward toward the lumen. Some implementations can also include a support coil running through the lumen. The support coil holds the lumen to be open to perfusion even in the early stages of balloon inflation. Methods of using the inflatable structures are also disclosed herein.

One embodiment includes a balloon catheter for insertion into a body lumen with blood flowing therethrough. The balloon catheter includes an elongate member and a plurality of balloons. The elongate member defines an inflation lumen and has a proximal and distal ends. The plurality of balloons are coupled to the distal end of the elongate member. The balloons are also connected in fluid communication with the inflation lumen of the elongate member. Advantageously, the balloons are arranged radially about a central axis so as to form a lumen. The lumen extends along the central axis when the balloons are inflated. The lumen is configured to pass blood and thus provide perfusion for downstream tissues of the patient. Each of the balloons includes a non-circular cross-sectional shape having at least two substantially straight side portions extending radially relative to the central axis. Each substantially straight side portion at least partially abuts the substantially straight side portion of an adjacent one of the balloons. In this manner, this adjacent arrangement guards against movement of the balloons and interruption of the perfusion lumen.

In another aspect, the balloon catheter may include a support coil. The support coil is coupled to the distal end of the elongate member and extends along the central axis within the lumen between the balloons. The support coil at least partially supports the balloons in both their crimped and inflated states. The support coil can include a dumbbell shape that has bulbous regions at its ends and a tubular central region. The support coil can include a large pitch at the bulbous end regions to facilitate blood passage therethrough. In addition, the balloon catheter may include an implant, such as a prosthetic heart valve, crimped over the balloons and the tubular central region of the support coil.

In another aspect, the straight side portions of the balloons may converge toward each other (in a cross-section) as they extend toward the central axis. This forms a wedge or keystone shape that stabilizes the balloons within the radially adjacent arrangement.

In other aspects, the non-circular cross-sectional shape may further comprise an inner portion and an outer portion. The inner portion extends between a radially inward end of the at least two substantially straight side portions. And, the outer portion extends between a radially outward end of the at least two substantially straight side portions. The inner portion can be positioned adjacent to the inner lumen so as to define a portion of the inner lumen. The outer portion can be longer than the inner portion and the cross-sectional shape can be a keystone shape.

In another aspect, the ends of the balloons can have spaces defined between them. The spaces connect the lumen between the balloons and the blood in the body lumen in fluid communication. For example, the ends of the balloons can taper to tubes with small enough diameters to define the spaces between them. The small diameter tubes can be combined into a manifold that is connected in communication with the inflation lumen of the elongate member. The manifold separates and distributes fluid for inflation of the balloons through their small diameter tubes.

In yet another aspect, the balloon catheter can include a plurality of interlocking mechanisms positioned between adjacent pairs of the balloons. The interlocking mechanisms can include, for example, corresponding U-shaped protrusions and recesses formed on the straight sides of the balloons.

The balloons catheter can also include a surrogate valve configured to block spaces defined between the ends of the balloons. This prevents backflow of blood through the lumen between the balloons. The surrogate valve can include a plurality of leaflets configured to extend over the spaces during backflow of blood. The leaflets can be further configured to deflect away from the spaces during forward flow of blood.

A method of using a balloon catheter of one embodiment includes extending an elongate member through an opening in a patient until a distal end of the elongate member reaches a procedure site. Fluid is flowed through an inflation lumen into a plurality of balloons coupled to the distal end of the elongate member at the procedure site. The balloons are inflated in a circumferentially adjacent arrangement to form a perfusion lumen extending along an axis about which the balloons are arranged. Stability of the balloon arrangement is maintained by abutting radially extending straight sides of the balloons against each other. Blood is perfused from one end of the circumferentially adjacent arrangement of balloons, through the perfusion lumen and to the other end of the circumferentially adjacent arrangement of balloons. In some implementations, the procedure site is a cardiovascular structure which is accessed transapically, transfemorally, or transaortically.

The method can also include, when inflating the balloons, defining spaces between the balloons at one end and at the other end of the arrangement and perfusing blood through the spaces into the perfusion lumen.

The method can further include expanding a prosthetic heart valve by exerting a force on a frame of the heart valve by inflating the balloons.

Also, the method can further include supporting the balloons on a helically wound coil extending through the perfusion lumen. The blood can also be perfused through the helically wound coil within the lumen.

DESCRIPTION OF DRAWINGS

FIG. 5A is a side view of an embodiment of an inflatable structure that includes a closed surrogate valve positioned at one end of the inflatable structure.

FIG. 5B is a side view of the inflatable structure of FIG. 5A wherein the surrogate valve is open.

DETAILED DESCRIPTION

Figure 1A:
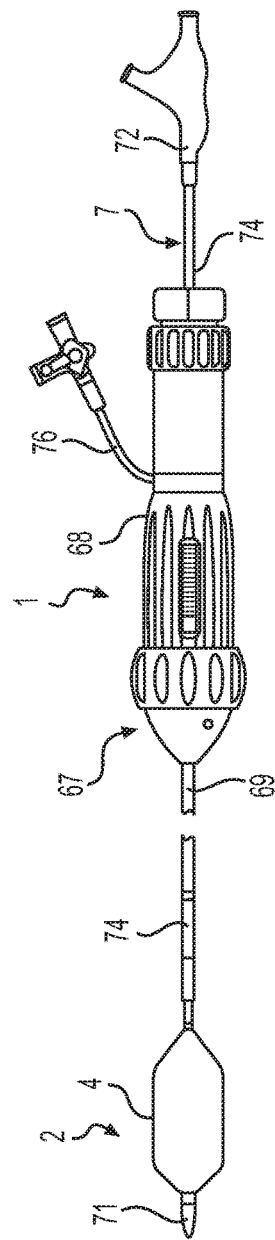
FIGS. 1A-1C show a delivery catheter assembly for delivering a prosthetic implant mounted on an inflatable structure.

The following description of certain examples of a medical apparatus (e.g., a balloon catheter assembly) should not be used to limit the scope of the medical apparatus. Other examples, features, aspects, embodiments, and advantages of the medical apparatus will become apparent to those skilled in the art from the following description. As will be realized, the medical apparatus is capable of additional aspects, all without departing from the spirit of the medical apparatus. Accordingly, the drawings and descriptions should be regarded as illustrative in nature and not restrictive.

For purposes of this description, certain aspects, advantages, and novel features of the embodiments of this disclosure are described herein. The described methods, systems, and apparatus should not be construed as limiting in any way. Instead, the present disclosure is directed toward all novel and nonobvious features and aspects of the various disclosed embodiments, alone and in various combinations and sub-combinations with one another. The disclosed methods, systems, and apparatus are not limited to any specific aspect, feature, or combination thereof, nor do the disclosed methods, systems, and apparatus require that any one or more specific advantages be present or problems be solved.

Features, integers, characteristics, compounds, chemical moieties, or groups described in conjunction with a particular aspect, embodiment or example of the invention are to be understood to be applicable to any other aspect, embodiment or example described herein unless incompatible therewith. All of the features disclosed in this specification (including any accompanying claims, abstract, and drawings), and/or all of the steps of any method or process so disclosed, can be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract, and drawings), or to any novel one, or any novel combination, of the steps of any method or process so disclosed.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Disclosed herein are inflatable structures for increasing perfusion during minimally-invasive cardiovascular procedures, increasing blood flow through the procedure site and/or reducing the need for rapid ventricular pacing. For example, the inflatable structures can be used in procedures for minimally invasive transcatheter heart valve replacement (TAVR), such as the procedures described in U.S. Pat. No. 7,175,656, which is hereby incorporated by reference in its entirety.

Other balloons have been designed to enhance perfusion during cardiovascular procedures by incorporating a central lumen through which blood can flow during the procedure. Current perfusion balloon designs, such as the one described in U.S. Pat. No. 7,951,111, include multiple balloons positioned radially around a central lumen. However, these balloons are cylindrical in shape, and can slip into the central lumen when the native annulus or valve applies a force upon the structure. Without being wed to theory, the inventors believe the movements are caused by a lack of contact between the balloons. The inflated cylindrical balloons are only in contact with each other in a line along the vertex of each diameter, making it easy for them to slip into the central lumen.

Generally, the inflatable structures disclosed herein facilitate the perfusion of blood through an anatomical structure, such as a heart valve, during a procedure. The inflatable structures are formed of a plurality of balloons arranged radially around a central opening. In particular, the plurality of balloons are arranged to form a lumen through which blood flows. The individual balloons of the plurality have a shape that facilitates the arrangement. For example, the individual balloons can have a keystone or wedge-like shape when viewed in cross section. The keystone or wedge-like shape limits the extent that individual balloons can move inward toward the lumen. Some embodiments can also include a support coil running through the lumen to maintain the open configuration of the lumen in the early stages of inflation of the balloons. Methods of using the inflatable structures are also disclosed herein.

Figure 1B:
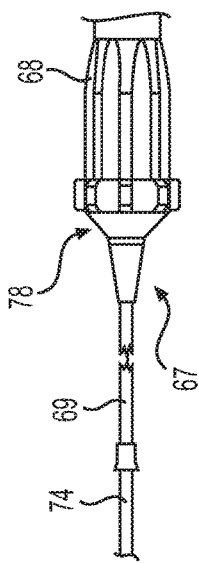
Figure 1C:
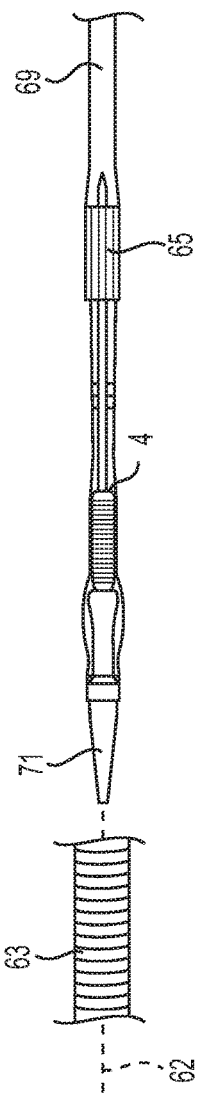

FIGS. 1A-1C illustrate a delivery catheter assembly 1 including a delivery sheath 63 for delivering a prosthetic implant 65, such as a prosthetic heart valve, to a patient. It should be understood that the delivery assembly 1 described herein is exemplary only, and that other similar delivery systems can of course be used. The delivery assembly 1 generally includes a steerable guide catheter 67 and a balloon catheter 7 extending through the guide catheter 67. The guide catheter 67 can also be referred to as a flex catheter, a delivery catheter, or a main catheter. The use of the term main catheter should be understood, however, to include flex or guide catheters, as well as other catheters that do not have the ability to flex or guide through a patient's vasculature.

The guide catheter 67 and the balloon catheter 7 illustrated in FIGS. 1A-1C are adapted to slide longitudinally relative to each other to facilitate delivery and positioning of prosthetic heart valve 65 at an implantation site in a patient's body, as described in detail below.

The guide catheter 67 includes a handle portion 68 and an elongated guide tube, or shaft, 69 extending from handle portion 68 (FIG. 1B). FIG. 1A shows the delivery apparatus without the guide tube 69 for purposes of illustration. FIG. 1B shows the guide tube 69 extending from the handle portion 68 over the balloon catheter 7. The balloon catheter 7 includes a proximal portion 72 (FIG. 1A) adjacent handle portion 68 and an elongated shaft 74 that extends from the proximal portion 72 and through handle portion 68 and guide tube 69. The handle portion 68 can include a side arm 76 having an internal passage which fluidly communicates with a lumen defined by the handle portion 68.

An inflatable balloon 4 is mounted at the distal end of balloon catheter 7. As shown in FIG. 1C, the delivery assembly 1 is configured to mount the prosthetic heart valve 65 in a crimped state proximal to the balloon 4 for insertion of the delivery assembly 1 and prosthetic heart valve 65 into a patient's vasculature, which is described in detail in U.S. Pat. No. 9,061,119 (U.S. application Ser. No. 12/247,846, filed Oct. 8, 2008), which is incorporated herein by reference. Because prosthetic heart valve 65 is crimped at a location different from the location of balloon 4 (e.g., in this case prosthetic heart valve 65 desirably is crimped proximal to balloon 4), prosthetic heart valve 65 can be crimped to a lower profile than would be possible if prosthetic heart valve 65 was crimped on top of balloon 4. This lower profile permits the surgeon to more easily navigate the delivery assembly 1 (including crimped prosthetic heart valve 65) through a patient's vasculature to the treatment location. The lower profile of the crimped prosthetic heart valve 65 is particularly helpful when navigating through portions of the patient's vasculature which are particularly narrow, such as the iliac artery. The lower profile also allows for treatment of a wider population of patients, with enhanced safety.

FIG. 1C also illustrates an expandable sheath 63 that extends over the guide tube 69 and the elongated shaft 74 of the balloon catheter 7. The expandable sheath 63 has a lumen to guide passage of the prosthetic heart valve 65. At a proximal end the expandable sheath 63 includes a hemostasis valve that prevents leakage of pressurized blood. The delivery assembly 1 also includes a hub 78 for connecting with the proximal end of the expandable sheath 63 (shown in FIG. 1B).

Generally, during use, the expandable sheath 63 is passed through the skin of patient (usually over a guidewire) such that the distal end region of the expandable sheath 63 is inserted into a vessel, such as a femoral artery, and then advanced to a wider vessel, such as the abdominal aorta. The delivery assembly 1 is then inserted into the expandable sheath 63, by first inserting the nose piece 71 through the hemostasis valve at the proximal end of the sheath 63. The steerable guide tube 69 is used to advance the balloon catheter 7 shaft 74 and prosthetic heart valve 65 through to and out of the end of the sheath 63. During the advancement of the prosthetic heart valve 65 through the sheath 63, the prosthetic heart valve 65 exerts a radially outwardly directed force on the sheath 63, causing it to expand. As the prosthetic heart valve 65 passes through the expandable sheath 63, the sheath 63 returns to its original, non-expanded configuration. When the delivery assembly 1 is at the desired procedure site, the prosthetic heart valve 65 is expanded (for example, by balloon inflation or by self-expansion) to implant the device in the patient's body. If the prosthetic heart valve 65 is positioned proximally to the balloon 4 to reduce the profile of the delivery assembly 1 (as shown in FIG. 1C), the balloon 4 can be retracted proximally with respect to the prosthetic heart valve 65, slipping into the lumen of the prosthetic heart valve 65 to enable balloon 4 inflation.

Figure 2A:
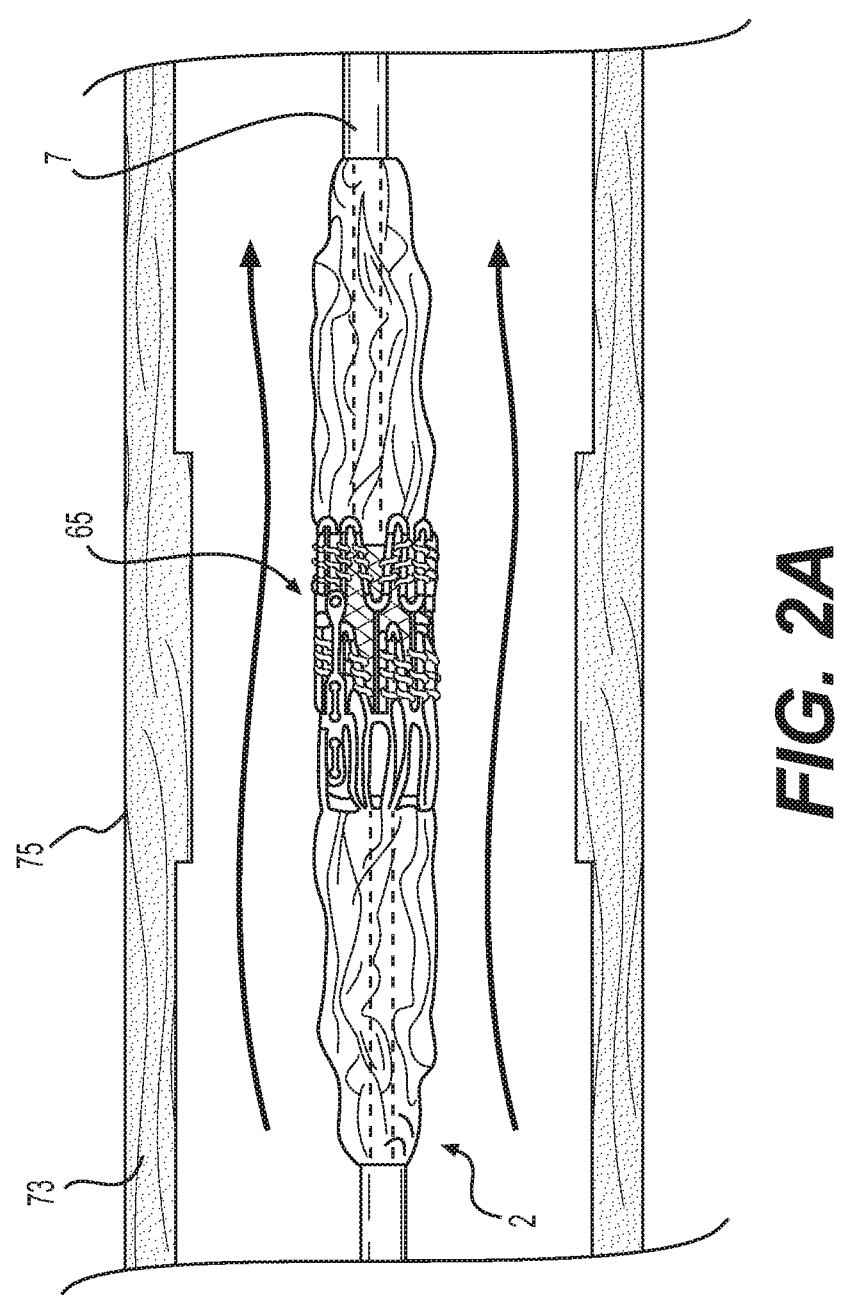
FIG. 2A is a side view of a prosthetic heart valve crimped on an inflatable structure and positioned within a cardiovascular procedure site.

FIG. 2A shows sectional view of a vessel containing the balloon catheter 7 with the prosthetic implant 65 mounted upon the inflatable structure 2. In this example, the prosthetic implant 65 is a prosthetic heart valve. The inflatable structure 2 and prosthetic heart valve 65 have been routed through the patient's blood vessel 73 for positioning within the patient's native cardiac valve annulus 75 schematically represented by thickened wall structure of the vessel. In FIG. 2A, the inflatable structure 2 is not yet inflated and the prosthetic heart valve 65 is not yet expanded. The large arrows indicate the flow of blood around the exterior surfaces of the inflatable structure 2 and the prosthetic heart valve 65. As it is not inflated, the balloon catheter 7 is not substantially interfering with blood flow.

Figure 2B:
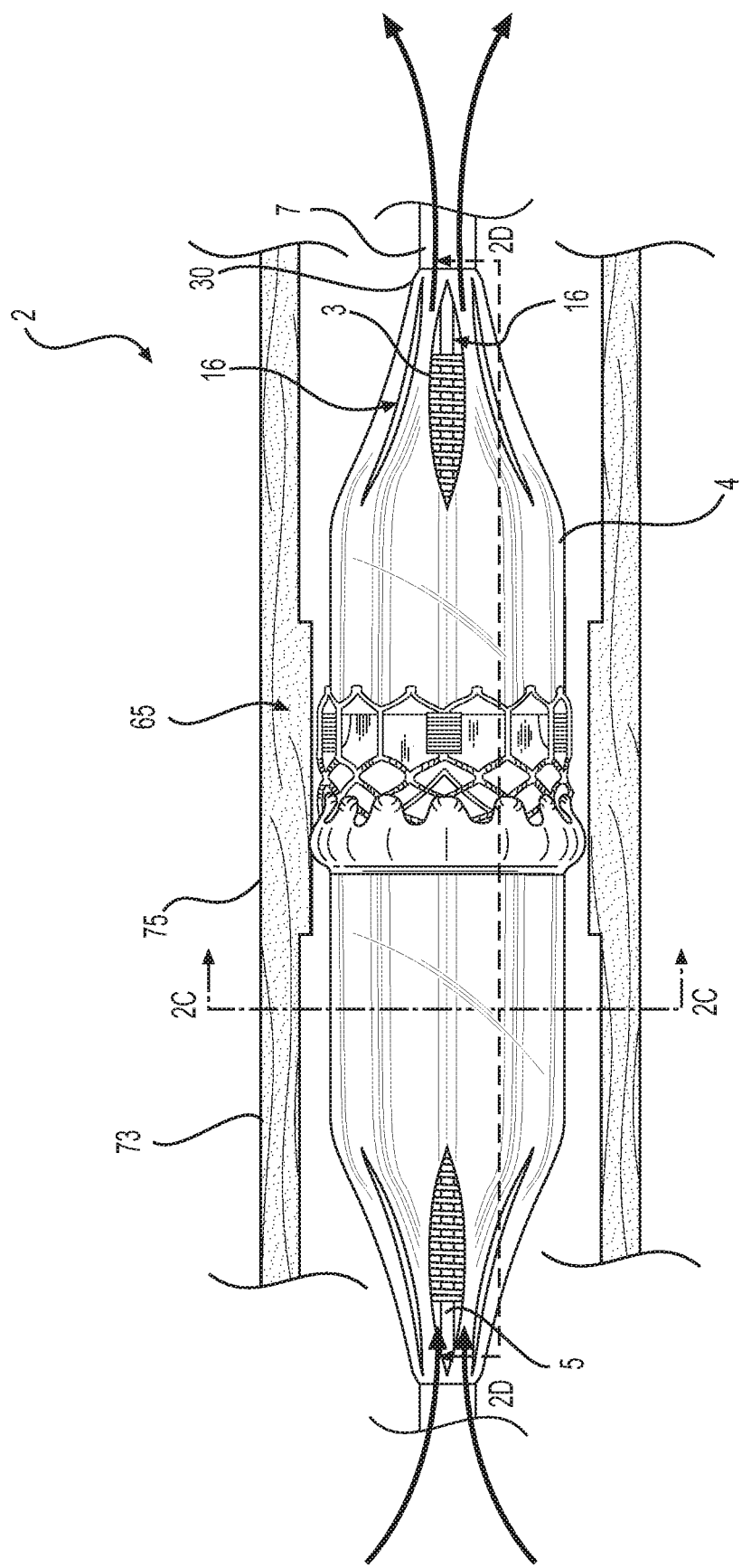
FIG. 2B is a side view of the inflated inflatable structure of FIG. 2A having expanded the prosthetic heart valve and dark arrows showing blood flow between the balloons of the inflatable structure.
Figure 2C:
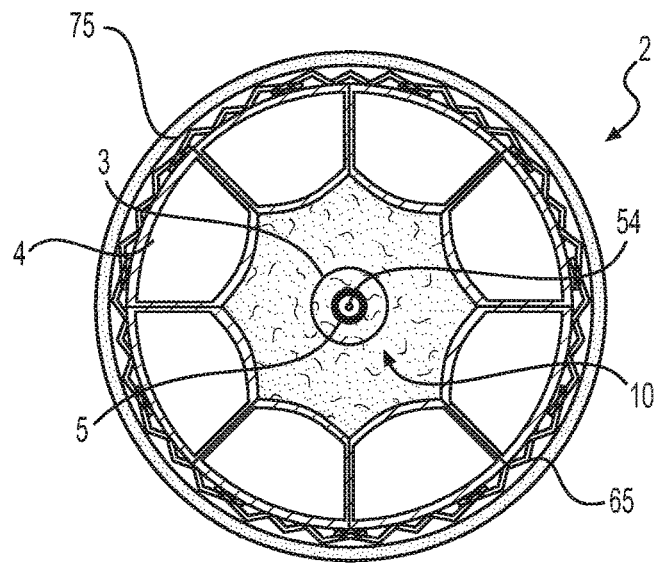
FIG. 2C is a cross sectional view of the inflated inflatable structure and expanded prosthetic heart valve taken along lines 2C-2C of FIG. 2B.

FIG. 2B shows another sectional view of the blood vessel 73 where the inflatable structure 2 has been inflated and the prosthetic heart valve 65 expanded within the native cardiac valve annulus 75. The inflatable structure 2 includes a plurality of radially arranged balloons 4 that form a lumen 10 that facilitates passage of blood flow even after inflation, as shown in the cross sectional view of FIG. 2C (taken along section line 2C-2C of FIG. 2B). In particular, FIG. 2C shows a shaded area in the lumen 10 representing blood flow through the lumen.

In FIG. 2B, the black arrows represent the blood flowing in between the ends of the balloons 4 which are spaced apart from each other in the inflatable structure 2. In particular, the balloons 4 have a smaller diameter, tapering structure at their ends that results in openings 16 between them providing access for the blood from outside the inflatable structure 2 to the central lumen 10.

Referring again to FIG. 2C, the balloons 4 can be shaped to facilitate preservation of their arrangement around the central lumen 10. In one aspect, the individual balloons 4 have a keystone or wedge-like cross-sectional shape that provide flat, radially oriented surfaces. These surfaces thus allow the balloons 4 to be arranged like pie pieces in a stable cylindrical configuration. Thus, advantageously, the keystone or wedge-like shape limits the extent that individual balloons 4 can move inward toward the lumen 10.

The inflatable structure 2 can be formed by placing the individual balloons 4 into parallel fluid communication with the distal end of the balloon catheter 7. For example, the proximal ends 30 of the individual balloons 4, each with an inflation lumen extending therethrough, are heat fused to the distal end of balloon catheter 7 to create a sealed joint. The sealed joint contains the bundled ends with the inflation lumens of each balloon 4 converging at the inflation lumen of the balloon catheter 7 into a manifold configuration so that fluid can move between the balloon catheter 7 and the inflation lumens of the balloons 4.

As shown in FIG. 2A, the balloons 4 can be collectively pleated and folded and crimped to a relatively small profile for delivery to the site of the procedure. For example, the crimped assembly can take on a profile that can be navigated through a range of vasculature and to the implantation site. The route of navigation can, for example, be transfemoral, transapical, or transaortic. Once the site of the procedure is reached, fluid (liquid or gas) is routed through balloon catheter 7, through the sealed joint at the distal end of the balloon catheter 7 which separates and directs the fluid into each of the plurality of balloons 4 individually. In some implementations of the method, the balloons 4 can inflate simultaneously for a uniform shape change, such as into the radially arranged inflatable structure 2 shown in FIG. 2C.

In some methods, an implantable device, such as a replacement heart valve or other implant, is positioned around the outer perimeter of the inflatable structure 2 during navigation through the patient's vasculature. Inflation of the inflatable structure 2 causes expansion of the heart valve or other implant. Other medical implants that can be delivered using the inflatable structure 2 include, for example, stents or annuloplasty devices. However, the inflatable structure 2 can be used without delivering an implant, for example, to widen a narrowed or blocked blood vessel or a stenosed native heart valve.

Figure 2D:
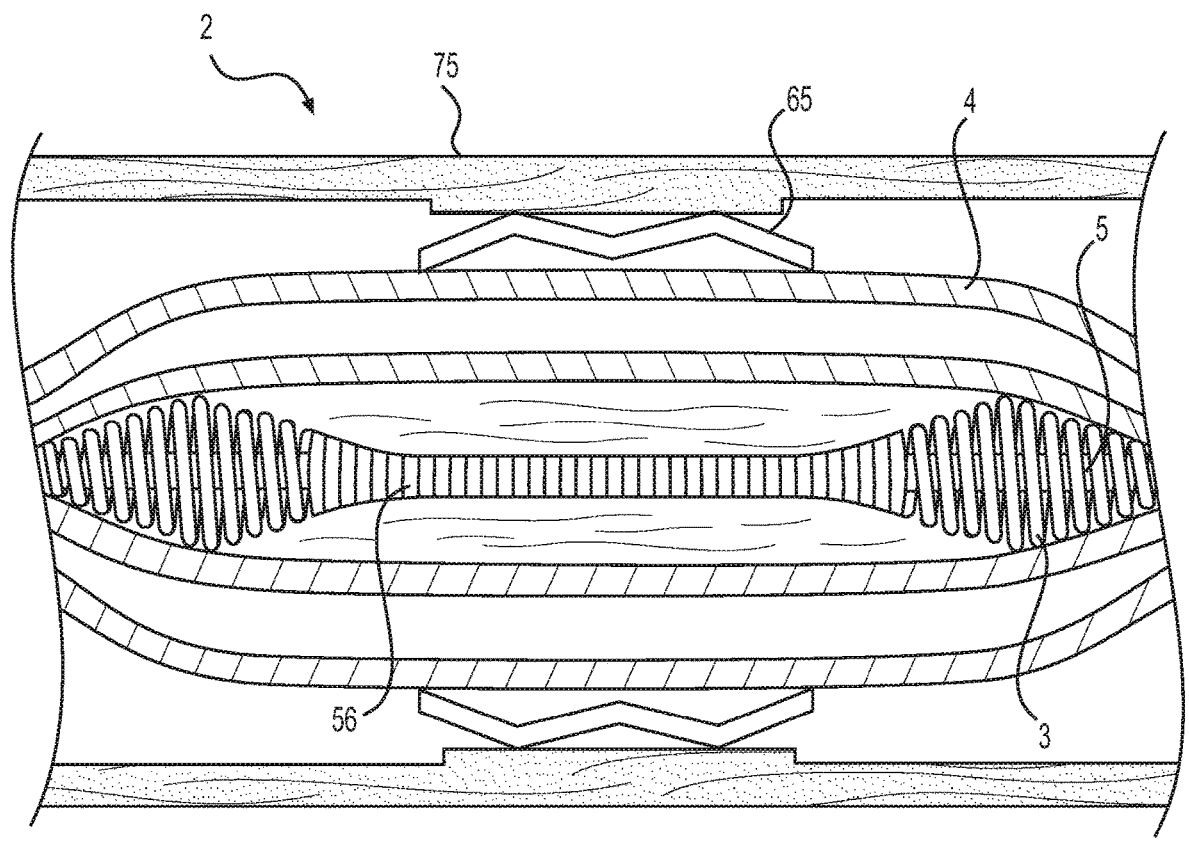
FIG. 2D is a cross sectional view of the inflated inflatable structure and expanded prosthetic heart valve taken along lines 2D-2D of FIG. 2B revealing a support coil extending longitudinally through the central area of the inflatable structure.

As shown in FIG. 2D, which is a partial cross-section of the inflatable structure 2 and prosthetic heart valve 65 taken along section line 2D-2D of FIG. 2B, the balloon catheter 7 can include a support coil 3 extending through the lumen 10 and over the guidewire 54. The support coil 3 has a wire or other linear, elongate material wound in a helical direction along the elongate axis 62 of the balloon catheter 7.

Figure 4:
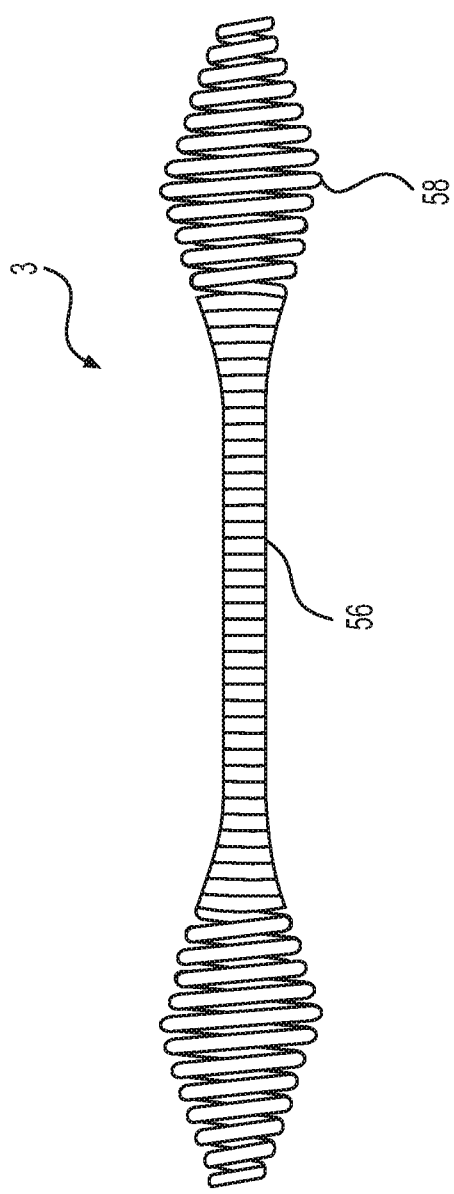
FIG. 4 is a side view of a support coil configured to extend longitudinally through the center of an inflatable structure.

FIG. 4 shows the support coil 3 separated from the inflatable structure 2. The support coil 3 has a dumbbell shape with a tubular central region 56 connecting bulbous end regions 58. The central region 56 of the support coil 3 has a dense pitch to provide support and narrower diameter than the end regions 58 to provide clearance for crimping on of the prosthetic heart valve 65. The central region's 56 smaller diameter thus helps to keep the overall profile of the balloon catheter 7 low when a prosthetic heart valve 65 is crimped or compressed thereon.

The diameter of each end region 58 thus increases progressively until reaching a maximum diameter and then decreases progressively back to approximately a diameter matching the diameter of the central region 56. The pitch of end regions 58 is less dense to facilitate blood flow through the wires and into the lumen 10. In addition, the larger diameter portions of end regions 58 help to prevent the ends of the balloons 4 from blocking blood flow through lumen 10. The inflatable structure's 2 lumen 10 is kept widened or flared at the ends by the progressively expanding diameter of the end regions 58.

Figure 3A:
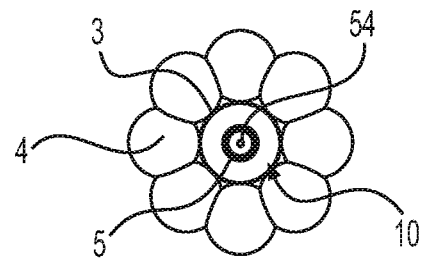
FIG. 3A is a schematic of an embodiment of an inflatable structure in a partially inflated state.
Figure 3B:
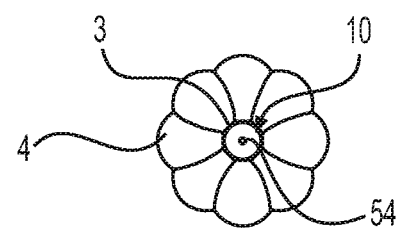
FIG. 3B is a schematic of another embodiment of an inflatable structure in a partially inflated state.

In some implementations, such as the one shown in FIG. 3B, the support coil 3 eliminates the need for guidewire tube 5. The support coil 3 therefore provides a lumen 10 and a guidewire passage without increasing the profile of the inflatable structure 2. For example, a support coil 3 with a 0.002 inch wall thickness can replace an inner guidewire tube 5 with a wall thickness of 0.007 inch and still have enough space for the passage of a guidewire 54 and blood perfusion during the initial stages of inflation.

The support coil 3 can be attached or coupled to the balloon catheter 7 in a number of ways. The end regions 58 of the support coil 3 can be glued, bonded, or heat fused either to the guidewire tube 5, the balloons 4, and/or the nose piece 71. During construction, the support coil 3 can be spaced from the guidewire tube 5 to maintain the lumen 10 of the inflatable structure 2 in an open configuration even prior to inflation of the balloons 4. The ability of the blood to perfuse the inflatable structure 2 through the support coil 3 prior to full inflation prevents the buildup of blood behind the structure 2. This increases the stability of the structure within the procedure site during the positioning phases of the procedure.

FIGS. 3A and 3B shows a cross-sectional schematic of the inflatable structure 2 of various embodiments during the early stages of inflation. Even a slight degree of inflation opens the lumen 10 to provide some passage for blood flow through the surrounding cardiovascular structure. For example, the opening of the lumen 10 enables blood to flow through the native heart valve and annulus during delivery and expansion of the prosthetic heart valve 65. The support coil 3 helps to maintain the lumen 10 in an open state during the early inflation stages, increasing the stability of the structure by preventing a buildup of blood and a concomitant upstream pressure increase.

Although a coil is illustrated in the figures, the support coil 3 could be replaced with other elongate, hollow structures that have a porosity to allow or facilitate perfusion. The support coil 3 could be replaced with a braided tube or a selectively cut tube. For example, the tube could be pierced or cut to have pores, holes or slots or combinations thereof.

Because perfusion begins at the initial stages of inflation, an interventionist has more time to complete the procedure than if blood perfusion were blocked by a conventional balloon. The interventionist can inflate the balloons 4 slowly and carefully for improved anchoring of the implant to the valve annulus. Slow inflation is advantageous because it gives physician time to accurately position the prosthetic heart valve 65. Slow inflation can also give time for calcified blood vessels to adjust to the round valve shape with minimal rupture of the surrounding tissue.

In some example methods, the transcatheter heart valve or other medical implant can be partially expanded by only partially inflating the inflatable structure 2. This provides an opportunity for the interventionist to reposition the implant prior to completing the inflation and anchoring the implant to the tissue. Perfusion of the procedural site occurs during the repositioning of the device which results in increased safety for the patient.

Some embodiments, such as those shown in FIGS. 5A-B, can include a surrogate valve 9 attached just proximal of the proximal ends of the balloons 4 for a transfemoral prosthetic aortic heart valve delivery procedure. The surrogate valve 9 mediates backflow of perfused blood in the distal direction (with respect to the catheter) upon inflation of the inflatable structure 2 and opening of the perfusion lumen 10. As shown in FIG. 5A, the surrogate valve 9 has a plurality of leaflets 77 and a base 79. The base 79 is positioned at the proximal end of the inflatable structure 2 and is attached to the balloon catheter 7. The leaflets 77 extend over the outside of the balloons 4 and in particular can block the openings 16 between the proximal balloon ends.

In other embodiments, the surrogate valve 9 can be positioned inside the lumen 10 formed by plurality of balloons 4 of inflatable structure 2. In this configuration, the leaflets 77 extend inside the openings 16.

The position of the surrogate valve 9 along the length of the balloon catheter 7 can also be varied depending upon the desired procedure. For example, for a transapical prosthetic aortic heart valve delivery procedure, primary perfusion flow would be desired in the distal direction (with respect to the catheter). Thus, the surrogate valve 9 can be positioned at the distal end of the inflatable structure 2—to collapse and block the openings 16 against retrograde flow in the proximal direction.

Regardless, the leaflets 77 of surrogate valve 9 take a closed position during diastole to prevent backflow of blood through the procedural site, as shown in FIG. 5A. During systole, the leaflets 77 of surrogate valve 9 are pushed open by the fluid pressure to permit perfusion of blood through the procedural site, as shown in FIG. 5B.

The surrogate valve 9 can be made with a range of thin, flexible and biologically compatible materials that can fold and bend under normal blood pressure. For example, the surrogate valve 9 can be constructed of the same material or structure as tissue-based or prosthetic valves intended for permanent implantation. In the illustrated embodiments, the leaflets 77 flare out into sets of three finger-like projections as they extend away from the base 79 and over the increasing diameter of the inflatable structure 2. Multiple leaflets 77 are arranged around the peripheral circumference of the inflatable structure 2.

Various additional embodiments of inflatable structures 2 are shown as simplified cross-sectional schematics in FIGS. 6A-E to illustrate additional stable configurations that facilitate the balloons 4 maintaining their collective inflatable structure 2 with the central lumen 10. In all of the FIGS. 6A-E, the plurality of balloons 4 are arranged radially around the central axis 8, forming the lumen 10. The number of balloons 4 can vary—with the illustrated embodiments being six or eight balloons 4. However, the inflatable structure 2 can be made up of as few as four balloons 4, or as many as 32 balloons 4.

Each of the balloons 4 of the inflatable structures 2 shown in the simplified cross sections of FIGS. 6A-E is non-circular in cross-section. Each of the cross-sections shown has two substantially straight side portions 6. The term "substantially straight side portion" is intended to describe a portion of an outer perimeter of a balloon 4 when viewed in cross-section. The substantially straight side portions 6 can also have a length in the axial direction. Some embodiments can have substantially straight side portions 6 along the entire length of the balloon 4. Other embodiments can have substantially straight side portions 6 along only a part of the length of the balloon 4.

When the inflated balloons 4 are radially arranged to form the larger inflatable structure 2, each substantially straight side portion 6 abuts a substantially straight side portion 6 of an adjacent balloon 4. This abutment prevents the balloons 4 from slipping into the lumen 10 of the inflatable structure 2. While the cross-sections shown in FIGS. 6A-E show balloons 4 with fully abutting substantially straight side portions 6, in other embodiments the substantially straight side portions 6 can abut only partially. Some embodiments include balloons 4 with more than two substantially straight side portions 6.

The cross section of each balloon 4 shown in FIGS. 6A-E also has an inner portion 12 and an outer portion 14 extending between the at least two substantially straight side portions 6. The length of the outer portion 14 is greater than the length of the inner portion 12. This difference in width contributes to the wedge shape and further prevents the balloons 4 from slipping into the lumen 10 of the inflatable structure 2.

Figure 6A:
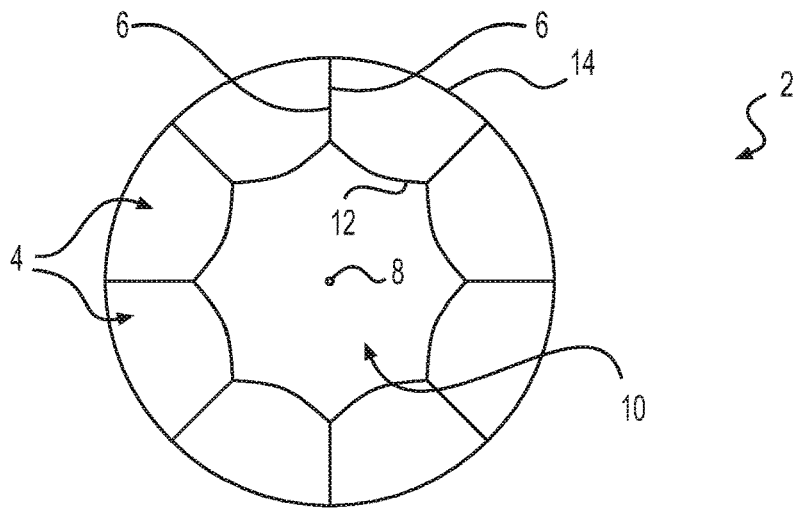
FIGS. 6A-6E are schematics of inflatable structure embodiments having balloons with non-circular cross-sections and that are arranged radially around a central axis.
Figure 6B:
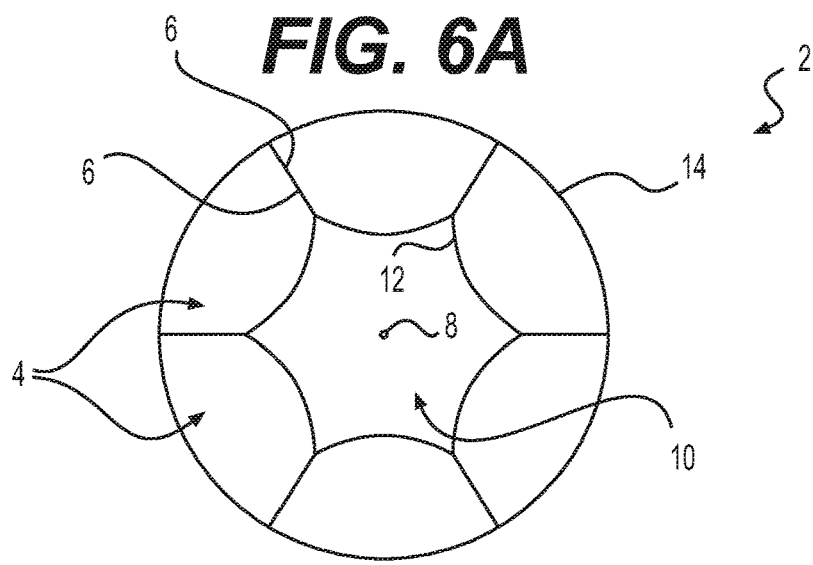
Figure 6C:
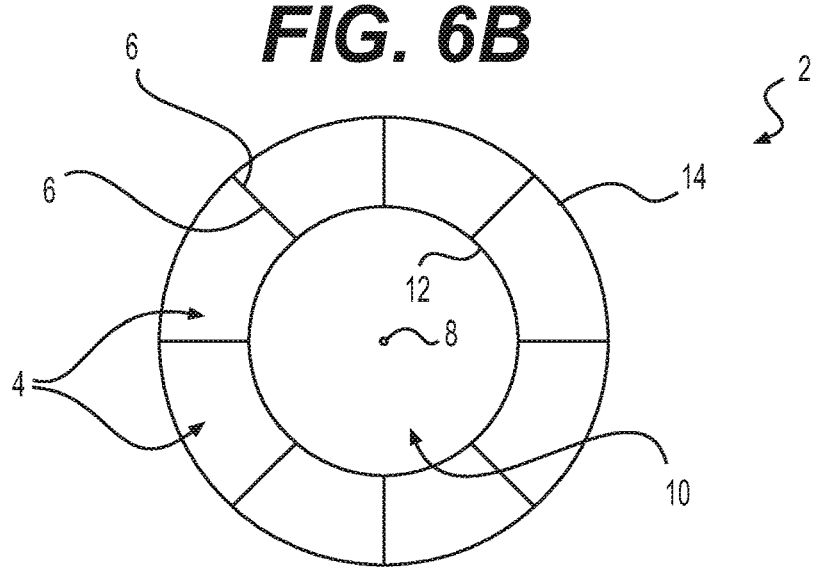
Figure 6D:
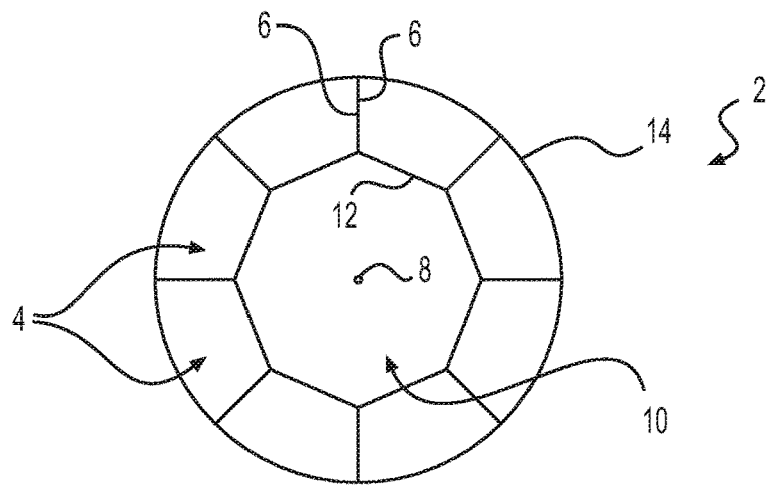
Figure 6E:
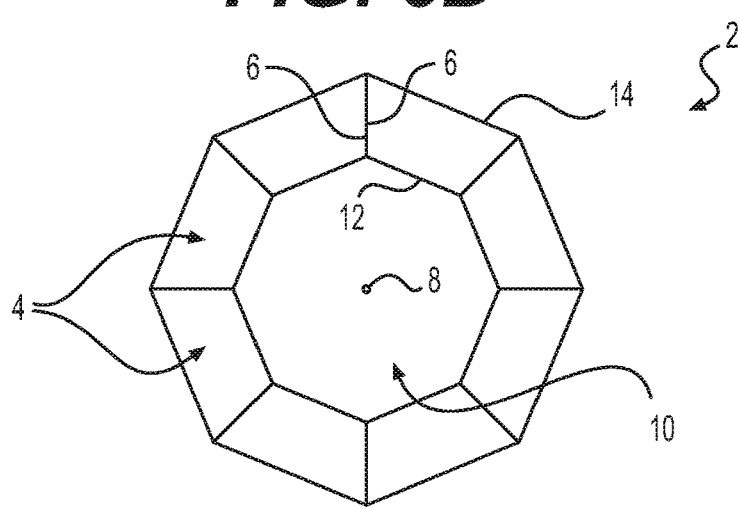

In some embodiments, the balloons 4 are polygonal in cross-section. For example, the balloons 4 can be trapezoidal in cross-section, as shown in FIG. 6E. In some embodiments, such as those shown in FIGS. 6A and 6B, the inner portion 12 of the balloon 4 curves inward into the lumen 10 of the inflatable structure 2. In some embodiments, such as those shown in FIG. 6C, the inner portion 12 curves outward away from the lumen 10. In some embodiments, such as those shown in FIGS. 6D and 6E, the inner portion 12 is substantially straight.

The outer portion 14 of the cross-section of the balloon 4 can curve outward away from the lumen 10 so that when they are assembled and inflated into the inflatable structure 2 it will approximate a cylinder, as shown in FIGS. 6A-D. The outer portion of the balloon 4 can also be substantially straight, as in FIG. 6E. The outer portion 14 can also curve inward toward the lumen 10 of the inflatable structure 2. Generally, then, the outer portion 14 can be shaped to accommodate the expected geometry of the vasculature or other body lumen it is meant to expand into.

The size of the inflatable structures 2 can also vary depending up on the particular application. For example, for prosthetic heart valve implantation, the perimeter measured around the outer surface of the inflatable structure 2 can range from about 16 to 33 millimeters, for example, 20, 23, 26, or 29 millimeters.

Figure 7:
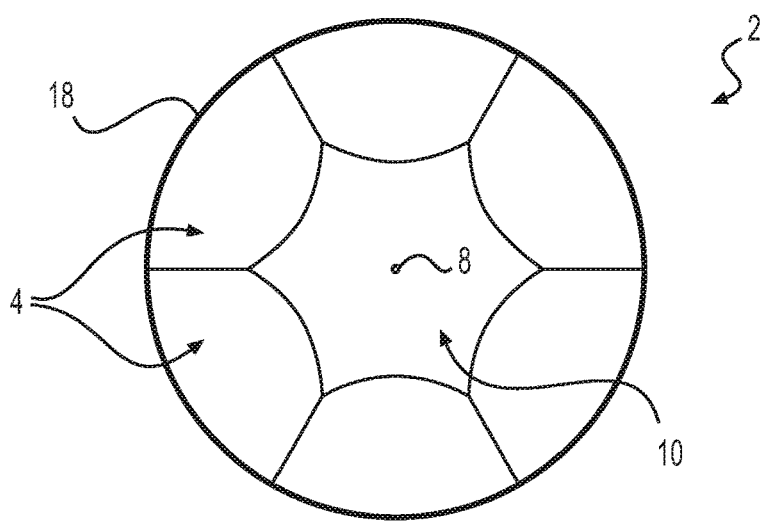
FIG. 7 is a schematic of another embodiment of an inflatable structure, including a layer of material positioned around the outer surface of a plurality of balloons.

Some embodiments, such as the one shown in FIG. 7, can include an outer layer of material 18 (such as a sock or sleeve) extending around the plurality of balloons 4. The outer layer of material 18 prevents balloons 4 from moving away from the central axis 8 and disrupting the radial arrangement of the plurality of balloons 4. The outer layer 18 can be formed of materials that are flexible and conforming, such as, for example, plastic film or woven mesh. Generally, the outer layer of material 18 is shaped to conform the balloons 4 or not interfere with the balloons 4 taking the desired shape of the inflatable structure 2. The thickness of the outer layer of material 18 can be 0.010 inches or less for relatively low impact on the profile of the delivery catheter assembly 1.

Figure 8:
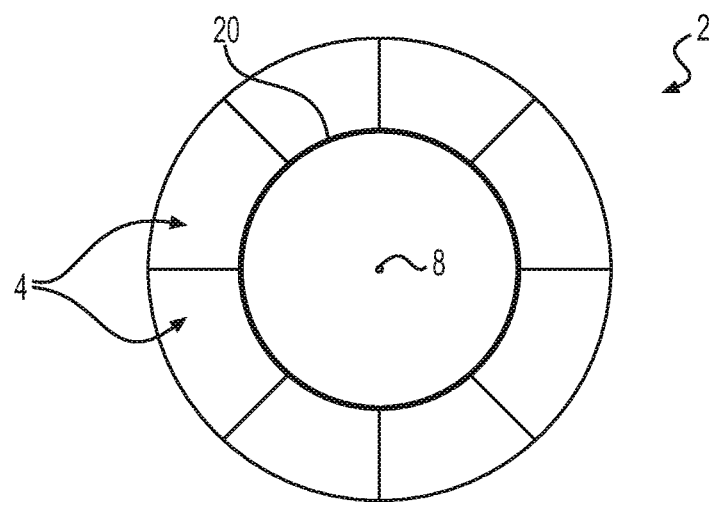
FIG. 8 is a schematic of another embodiment of an inflatable structure, including a layer of material positioned between the lumen and a plurality of balloons.

Some embodiments, such as the one shown in FIG. 8, include an inner layer of material 20 that separates the inner faces of the balloons 4 from the lumen 10 of the inflatable structure 2. The inner layer of material 20 prevents balloons 4 from moving inward toward the central axis 8 and disrupting the radial arrangement of the plurality of balloons 4. The inner layer of material 20 can be formed of materials that are flexible and conforming, such as, for example, plastic film or woven mesh. The thickness of the inner layer of material 20 can be 0.010 inches or less to minimize reduction in the size of the lumen 10.

Figure 9:
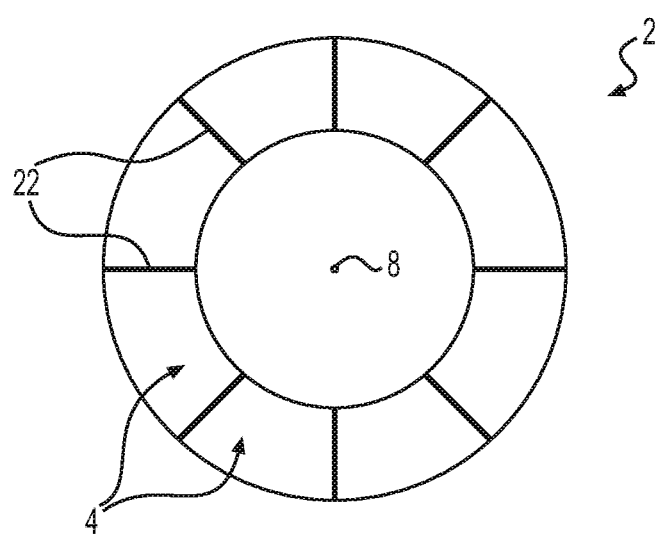
FIG. 9 is a schematic of another embodiment of an inflatable structure, including an attachment mechanism positioned between pairs of balloons.

The inflatable structure 2, as shown schematically in FIG. 9, can include an attachment mechanism 22 positioned between the substantially straight side portions 6 of balloons 4. The attachment mechanism 22 can be, for example, an adhesive, or string, a ribbon, a suture, a wire, or roughened surfaces, or any other mechanism that stabilizes the radial arrangement of the balloons 4. The attachment mechanism 22 can be positioned between the sides of the balloon 4, or it can span the inner faces or outer faces of the balloons 4. The attachment mechanism 22 stabilizes the radial arrangement of the balloons 4 around the central axis 8 by further reducing a balloon's movement relative to the other balloons 4.

Figure 10A:
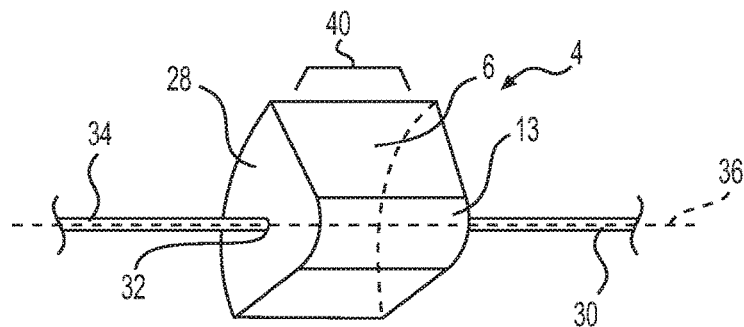
FIGS. 10A-10D are schematics of individual balloons from various inflatable structure embodiments.

FIGS. 10A-D show perspective views of various types of balloons 4 separated from the larger inflatable structure 2. In particular, the balloons 4 of FIGS. 10A-D have varied shapes. FIG. 10A, for example, shows the balloon 4 having an inner face 13 that curves into the lumen 10 when assembled with other similar balloons 4 into the inflatable structure 2. When assembled with other similarly constructed balloons 4 into the inflatable structure 2, the inflatable structure 2 would have a cross-section reminiscent of FIG. 6A.

The balloon 4 also has a first end portion and a second end portion having substantially flat surfaces 28. A balloon inflation leg 34 extends away from a first opening 32 on the first end portion of the balloon 4 and from a second opening (not shown) on the second end portion of the balloon 4. In some embodiments, the balloon openings lie along a common axis extending through a center of the flat surfaces 28. Alternatively, the balloon openings can be spaced away from the center or a common longitudinal axis depending upon inflation and manufacturing concerns. The openings and inflation leg 34 provide conduits for inflation fluid to flow from the inflation lumen 10 of the catheter to the interior of the balloon 4 and in reverse for deflation.

Figure 10B:
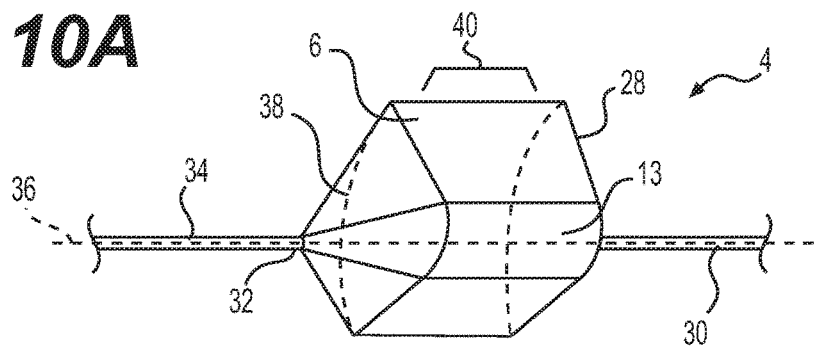

FIG. 10B shows another embodiment of the balloon 4 separate from the larger inflatable structure 2. The balloon 4 of FIG. 10B also has the inner face 13 that curves into the lumen 10 of the larger inflatable structure 2. When assembled with other balloons 4 into the inflatable structure 2, the inflatable structure 2 would have a cross-section reminiscent of FIG. 6A. The balloon 4 also has a first end portion and a second end portion. The first end portion has a taper 38 that narrows extending away from the body portion 40 of the balloon 4. One end portion can have the taper 38 while the other has a substantially flat surface 28, as shown in FIG. 10B. Or, both end portions can have the taper 38. The taper can mediate the material stress in the balloon 4 caused by a more sudden transition in diameter.

Figure 10C:
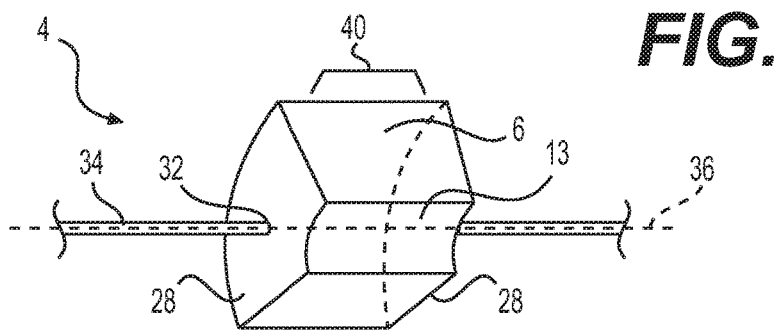
Figure 10D:
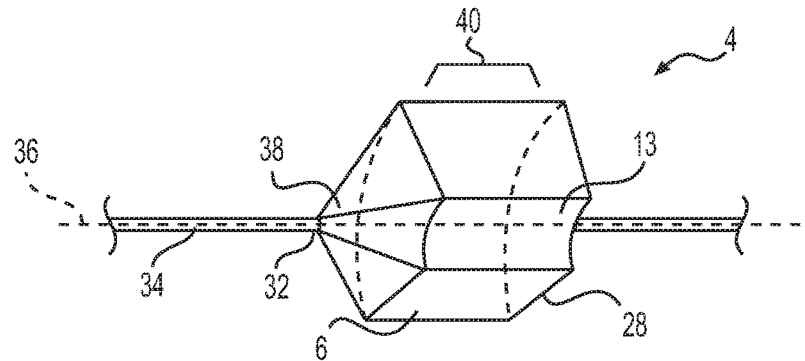

FIGS. 10C-D show embodiments of balloons 4 with inner faces 13 that curve outward away from the lumen 10 of the larger inflatable structure 2. When assembled with other balloons 4 into the inflatable structure 2, the inflatable structure 2 would have a cross-section reminiscent of FIG. 6C. The balloon 4 of FIG. 10C has end portions with substantially flat surfaces 28. The balloon 4 of FIG. 10D has a first end portion with the taper 38, and a second end portion with a substantially flat surface 28.

Body portions 40 of the balloon embodiments shown in FIGS. 10A-10D have consistent cross-sectional areas along the working lengths of the balloons 4. However, in some embodiments, the cross-sectional area of the body portion 40 changes along the length of the balloon—such as by having a tapering body portion. The cross-sectional area of the body portion 40 can be larger than that of a tapered end portion, as seen in FIGS. 10B and 10D. The cross-sectional area of the body portion 40 can also be less than the largest cross-sectional area of an end portion so as to form an enlarged end to help anchor the balloons 4 or to retain the implant. These variations can also be configured to fit the different expected sizes the body lumens or implants.

In some embodiments, the inflatable structure 2 can be made up of multiple groupings of balloons 4 positioned along the central axis of the larger inflatable structure 2. For example, a first grouping or balloons 4 can be arranged radially about the central axis 8 of the larger inflatable structure 2, and a second grouping of balloons 4 can be arranged radially about the central axis 8 and positioned longitudinally adjacent to the first grouping of balloons 4. This allows, for example, building up the inflatable structure 2 to a desired diameter and length.

Figure 11A:
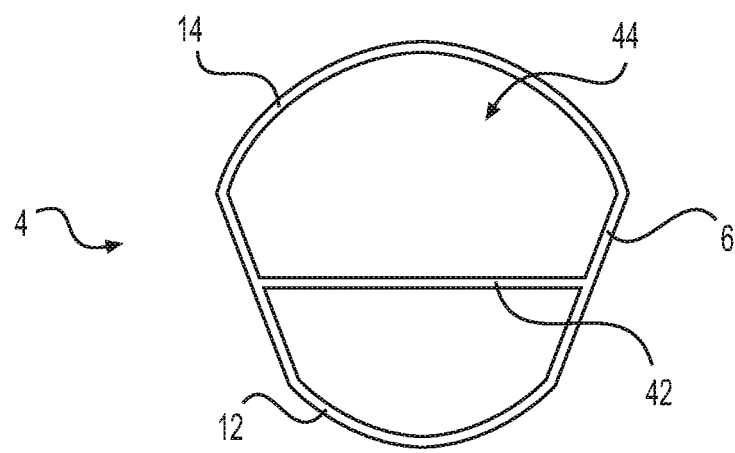
FIG. 11A is a schematic of an individual balloon with interior webbing, wherein the individual balloon can be part of a larger inflatable structure.
Figure 11B:
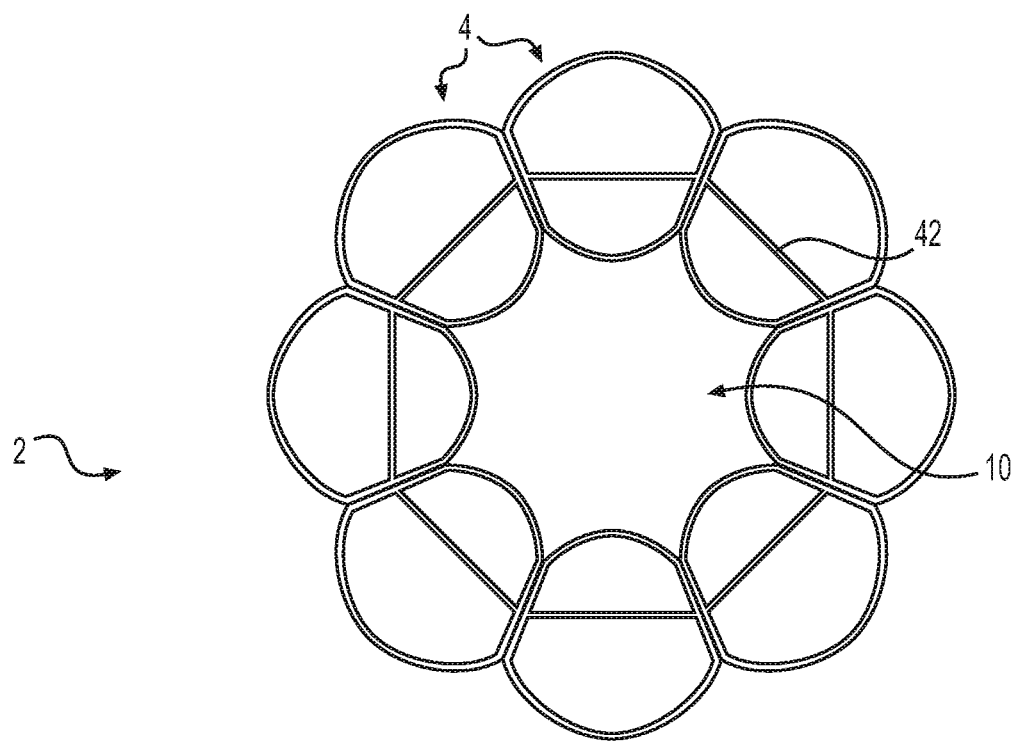
FIG. 11B is a schematic of an embodiment of an inflatable structure including the balloon of FIG. 11A.

FIG. 11A shows a cross-section of another embodiment wherein the balloon 4 has webbing 42 extending through the interior portion 44 of the balloon 4. In particular, the webbing 42 extends between and connects straight side portions 6. FIG. 11B shows a cross-section of another inflatable structure 2 embodiment formed from balloons 4 with webbing 42 extending through their interior portions 44.

Figure 12A:
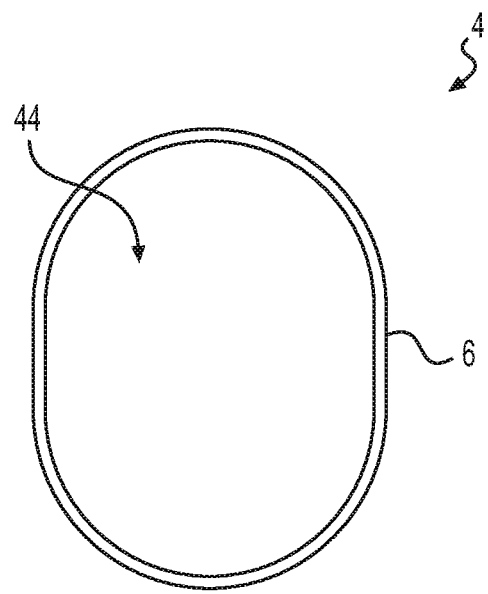
FIG. 12A is a schematic of an uninflated balloon.
Figure 12B:
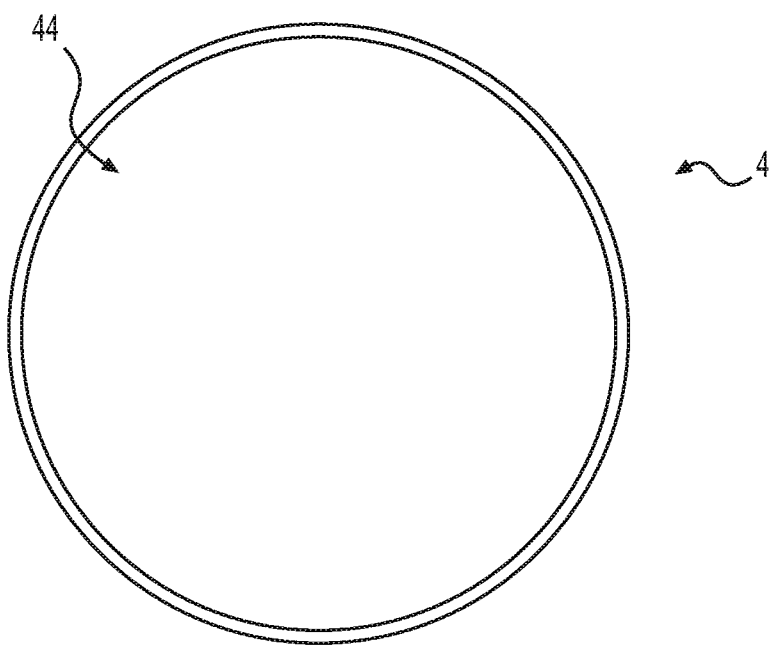
FIG. 12B is a schematic of the balloon of FIG. 12A, after inflation.
Figure 13A:
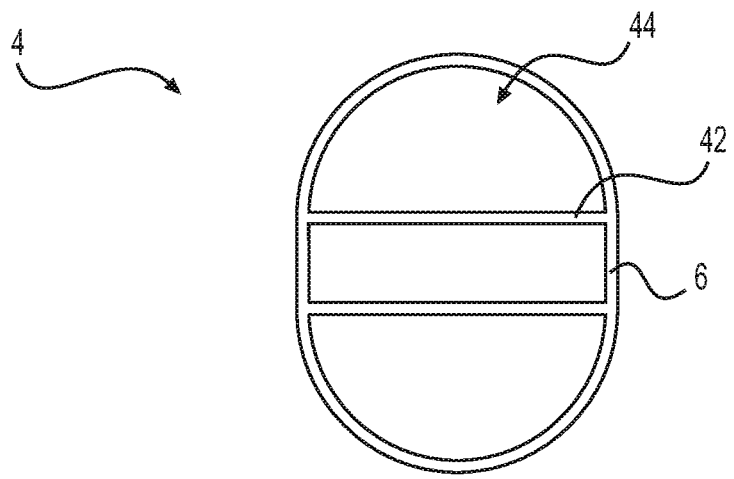
FIG. 13A is a schematic of an uninflated balloon with webbing.
Figure 13B:
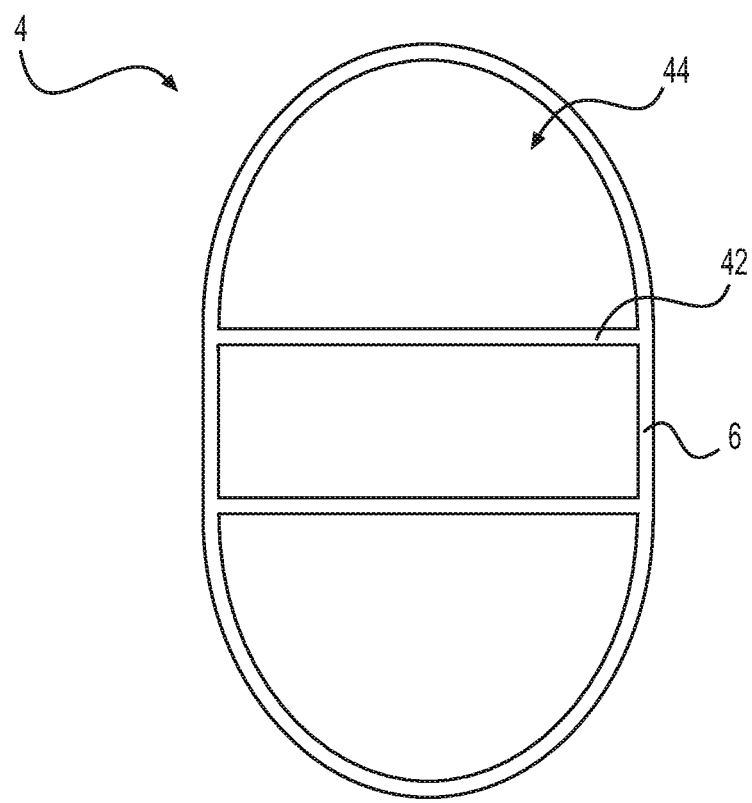
FIG. 13B is a schematic of the balloon of FIG. 13A, after inflation.

Advantageously, the webbing 42 facilitates the retention of side portions 6 in a substantially straight configuration upon inflation. For example, FIG. 12A shows a cross section of an uninflated balloon 4 and FIG. 12B shows a cross section of the same balloon 4 after inflation. Upon inflation, the walls of the balloon 4 expand and the cross section becomes circular in shape. Meanwhile, the uninflated balloon 4 shown in FIG. 13A has webbing 42 extending through the interior portion 44. Upon inflation, as shown in FIG. 13B, the side portions 6 of the balloon retain their substantially straight configuration. The balloon 4 can have more than one piece of webbing 42, such as the two webs 42 of FIGS. 13A and 13B, extending through its interior portion 44. Additional webs 42 can be employed depending upon the desired allocation of their effect on the balloon shape. Various portions of the walls of the balloons 4 can be shaped—made flat or pinched, for example—through use of more webs to meet the varied shapes of patient lumens and/or of the implantable devices.

Figure 14A:
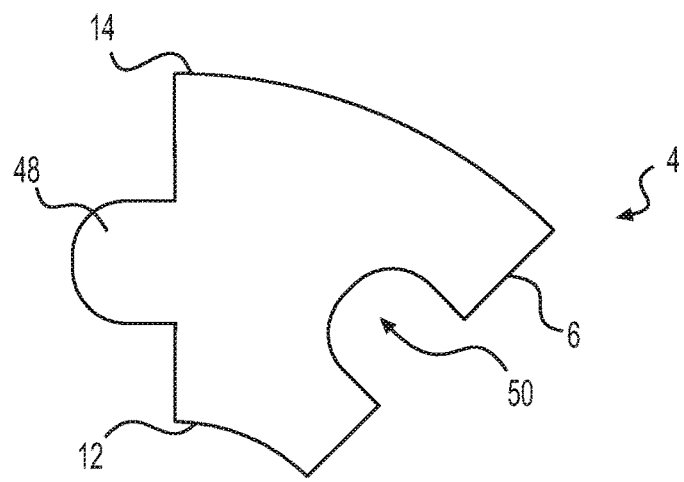
FIG. 14A is a schematic of a balloon including an interlocking mechanism.
Figure 14B:
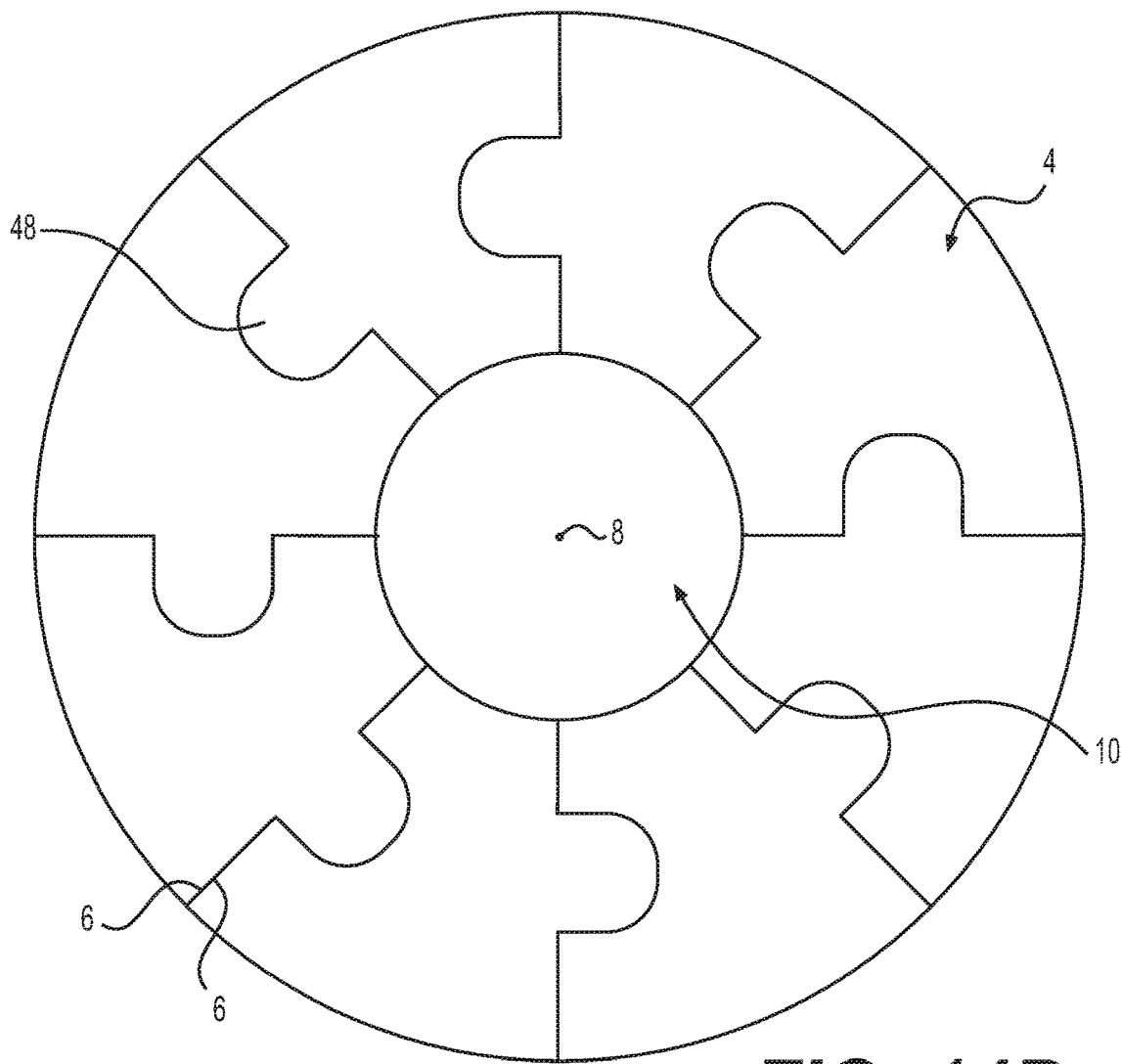
FIG. 14B is a schematic of an embodiment of an inflatable structure including the balloon of FIG. 14A.

FIGS. 14A-B schematically depict an inflatable structure 2 including a plurality of balloons 4 each including interlocking mechanisms that stabilize adjacent balloons 4 to limit movement. The interlocking mechanism includes a protrusion 48 extending from a substantially straight side portion 6 of a first balloon 4. The protrusion 48 is shaped to nest within a recession 50 in the substantially straight side portion 6 of an adjacent, second balloon 4. For example, the protrusion 48 in FIG. 14A has a U-shape with the rounded end pointing away from the straight side portion 6. Correspondingly, the recession 50 has a U-shape with the rounded end pointing into the balloon 4. The U-shape can be an extruded shape that extends the length of the balloon 4 body or it can be a cylinder topped with a rounded dome and corresponding features on the recession 50.

Though the embodiment of FIGS. 14A-B has only one protrusion and recession per balloon 4, a balloon 4 can have multiple protrusions 48 corresponding to multiple recessions 50 on an adjacent balloon 4. The multiple protrusions 48 and recessions 50 can be distributed radially between the adjacent balloon 4 surfaces. For example, in a cross-section such as the schematic of FIG. 14B, two, three or more protrusions 48 can be at radially spaced intervals along the adjacent side portions 6 of the balloons 4. Multiple protrusions 48 and recessions 50 can also be distributed along the length of the balloons 4.

The shapes and dimensions of the protrusion 48 and recession 50 can vary based on factors such as desired security and ease of interlock. The interlocking mechanism shown in FIGS. 14A-B is dome shaped, which advantageously provides a large surface area for interlock of the balloons 4. However, protrusion 48 and recession 50 could be shaped differently and still function to limit the movement of balloons 4 relative to each other. For example, the opposing side portions 6 of adjacent balloons 4 can have complementary zig zag sections configured to engage one another.

Figure 15:
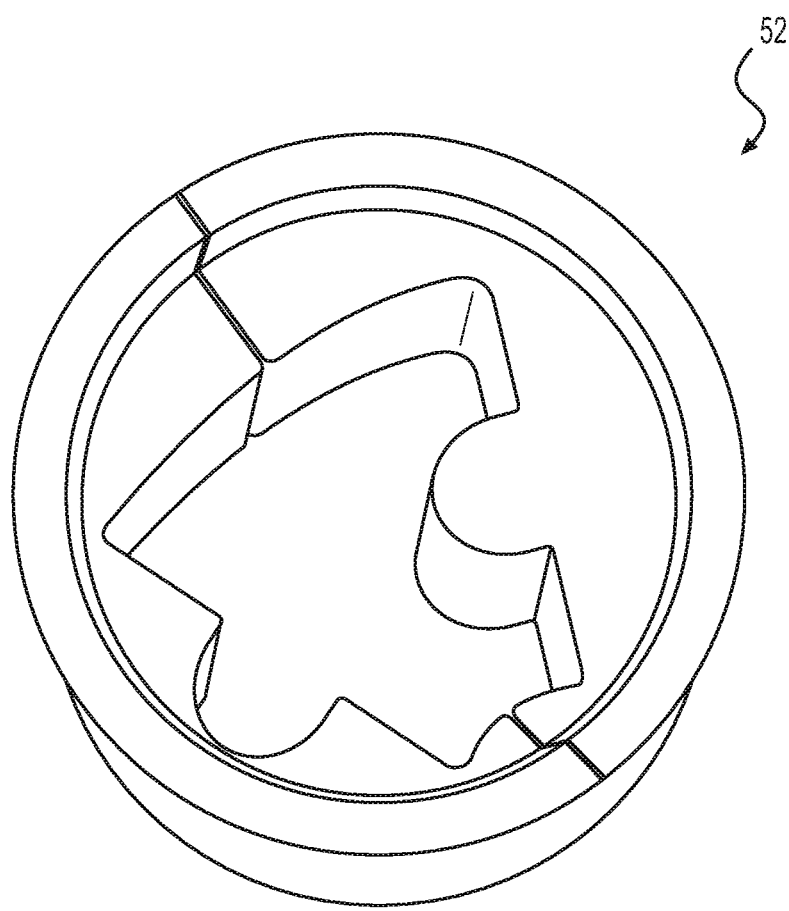
FIG. 15 is a schematic of a mold used to make the balloon of FIG. 14A.

FIG. 15 shows a balloon mold 52 for fabricating the balloons 4 with interlocking mechanisms. The balloon mold 52 is constructed of two halves. The halves are joined together to form a cavity using, for example, press-fit pins and/or set screws. The cavity of the balloon mold 52 then has a shape defining the curved shapes of the inner portion 12 and outer portion 14, the straight side portions 6 and the corresponding U-shaped protrusion 48 on one side and recession 50 on the other. The wall thickness is set by having a smaller profile but correspondingly shaped mandrel inserted through the cavity of the balloon mold 52. The mandrel's size difference defines the wall thickness of the balloon 4—a smaller mandrel results in a bigger wall thickness.

An extrusion process is performed by pressurizing a liquid polymer within a closed housing or tube having an opening within which is secured the periphery of the balloon mold 52 with the mandrel extending therethrough. As the pressure builds the liquid polymer pushes over the mandrel and under the edges defining the cavity to create a correspondingly shaped wall structure for the balloon. This shape can be then sealed off on its ends through conventional processes.

Balloon molds can be made from materials suited to withstand the high temperatures necessary to form plastic balloons. The materials can include, but are not limited to beryllium copper and/or copper alloys. Balloon molds can be fabricated using machining, 3D printing, or laser cutting to create the desired cavity shape for the particular balloon application.

Although the disclosure has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments. In addition, while a particular feature of the disclosure may have been described above with respect to only one or more of several illustrated embodiments, such feature may be combined with one or more other features of the other embodiments, as may be desired and advantageous for any given or particular application.

What is claimed is:

1. A balloon catheter for insertion into a body lumen with blood flowing therethrough, the balloon catheter comprising:
   an elongate member defining an inflation lumen, the elongate member having a proximal end and a distal end, a plurality of balloons coupled to the distal end of the elongate member and connected in fluid communication with the inflation lumen of the elongate member, and a plurality of interlocking mechanisms, wherein one interlocking mechanism is positioned between each adjacent pair of the balloons,
   wherein the balloons are arranged circumferentially about a central axis so as to form an additional lumen extending along the central axis and wherein the lumen is configured to allow passage of the blood therethrough, wherein each of the balloons comprises a non-circular cross-sectional shape having at least two substantially straight side portions extending radially relative to the central axis, and wherein each substantially straight side portion at least partially abuts the substantially straight side portion of an adjacent one of the balloons.

2. The balloon catheter of claim 1, further comprising a support coil coupled to the distal end of the elongate member, the support coil extending along the central axis within the additional lumen and at least partially supporting the balloons.

3. The balloon catheter of claim 2, wherein the support coil has a dumbbell shape with a tubular central region extending between opposing bulbous end regions.

4. The balloon catheter of claim 3, wherein a pitch of the support coil at the bulbous end regions is greater than a pitch of the support coil at the tubular central region to facilitate passage of the blood therethrough each of the bulbous end regions.

5. The balloon catheter of claim 4, further comprising a prosthetic heart valve crimped over the balloons and the tubular central region of the support coil.

6. The balloon catheter of claim 1, wherein the each of the at least two substantially straight side portions converge toward each other extending toward the central axis.

7. The balloon catheter of claim 1, wherein the non-circular cross-sectional shape of each of the balloons further comprises an inner portion extending between a radially inward end of each of the at least two substantially straight side portions and an outer portion extending between a radially outward end of each of the at least two substantially straight side portions.

8. The balloon catheter of claim 7, wherein the inner portion defines a portion of the additional lumen.

9. The balloon catheter of claim 8, wherein the outer portion is longer than the inner portion and wherein the cross-sectional shape is a keystone shape.

10. The balloon catheter of claim 1, wherein ends of the balloons have openings defined therebetween, the openings establishing fluid communication between the additional lumen and the blood in the body lumen.

11. The balloon catheter of claim 10, wherein the ends of the balloons taper to small diameter tubes and are combined into a manifold in communication with the inflation lumen of the elongate member.

12. The balloon catheter of claim 1, wherein each of the interlocking mechanisms includes a protrusion and a recess, the recess configured to receive the protrusion.

13. The balloon catheter of claim 12, wherein the protrusion has a U-shape and the recess has a corresponding U-shape.

14. The balloon catheter of claim 1, further comprising a surrogate valve configured to block openings defined between ends of the balloons to prevent backflow of blood.

15. The balloon catheter of claim 14, wherein the surrogate valve includes a plurality of leaflets configured to extend over the openings during backflow of blood.

16. The balloon catheter of claim 15, wherein the leaflets are further configured to deflect away from the openings during forward flow of blood.

17. The balloon catheter of claim 1, wherein at least one of the balloons includes at least one web extending between and connected to the at least two substantially straight side portions.

18. A method of using a balloon catheter, the method comprising:
   flowing fluid through an inflation lumen into a plurality of balloons coupled to a distal end of an elongate member;
   wherein each of the balloons comprises a non-circular cross-sectional shape having at least two substantially straight side portions extending radially relative to a central axis, and wherein each substantially straight side portions at least partially abut the substantially straight side portion of an adjacent one of the balloons;
   positioning the balloons in a circumferentially adjacent arrangement and inflating the balloons to form a perfusion lumen extending along the central axis about which the balloons are arranged;
   maintaining stability of the balloons by abutting radially extending sides of the balloons against each other;
   a plurality of interlocking mechanisms, wherein one interlocking mechanism is positioned between each adjacent pair of the balloons; and
   perfusing a second fluid from one end of the circumferentially adjacent arrangement of balloons, through the perfusion lumen and to another end of the circumferentially adjacent arrangement of balloons.

19. The method of claim 18, further comprising supporting the balloons on a helically wound coil extending through the perfusion lumen.

* * * * *